United States Patent [19]

Withers, Jr. et al.

[11] Patent Number: 4,670,619

[45] Date of Patent: Jun. 2, 1987

[54] METHANE CONVERSION PROCESS

[75] Inventors: Howard P. Withers, Jr., Douglassville; C. Andrew Jones, Newtown Square; John J. Leonard, Springfield; John A. Sofranko, Malvern; Anne M. Gaffney, West Chester, all of Pa.

[73] Assignee: Atlantic Richfield Company, Los Angeles, Calif.

[21] Appl. No.: 738,111

[22] Filed: May 24, 1985

Related U.S. Application Data

[63] Continuation-in-part of Ser. No. 600,656, Apr. 16, 1984, Pat. No. 4,523,049, and a continuation-in-part of Ser. No. 600,670, Apr. 16, 1984, Pat. No. 4,523,050.

[51] Int. Cl.$^4$ .................................................. C07C 2/00
[52] U.S. Cl. ..................................... 585/500; 585/415; 585/417; 585/418; 585/541; 585/654; 585/656; 585/658; 585/661; 585/943
[58] Field of Search ............... 585/500, 943, 415, 417, 585/418, 541, 654, 656, 658, 661

[56] References Cited

U.S. PATENT DOCUMENTS

| | | | |
|---|---|---|---|
| 4,443,648 | 4/1984 | Jones et al. | 585/417 |
| 4,523,049 | 6/1985 | Jones et al. | 585/415 |

FOREIGN PATENT DOCUMENTS 3237079  4/1984  Fed. Rep. of Germany ...... 585/500

OTHER PUBLICATIONS

Keller and Bhann, "Synthesis of Ethylene Via Oxidative Coupling of Methane", J. of Catalysis, 73 9–19 (1982).

Primary Examiner—William R. Dixon, Jr.
Assistant Examiner—Cynthia A. Prezlock
Attorney, Agent, or Firm—Craig E. Larson

[57] ABSTRACT

An improved method for converting methane to higher hydrocarbon products by contacting a hydrocarbon gas comprising methane, an oxygen-containing gas and a reducible metal oxide under conditions effective to produce higher hydrocarbon products and water, the improvement which comprises conducting the contacting in the presence of at least one stabilizer selected from the group consisting of chalcogens and compounds thereof.

18 Claims, No Drawings

METHANE CONVERSION PROCESS

CROSS REFERENCE TO RELATED APPLICATION

This application is a continuation-in-part of U.S. patent application Ser. No. 600,656 now U.S. Pat. Nos. 4,523,049 and 600,670, now U.S. Pat. No. 4,523,050 both filed Apr. 16, 1984. The entire content of each of these applications incorporated by reference.

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins such as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See U.S. Pat. Nos. 4,443,649; 4,444,984; 4,443,648; 4,443,645; 4,443,647; 4,443,644; and 4,443,646.

Commonly-assigned U.S. patent application Ser. No. 522,935, filed Aug. 12, 1983, discloses and claims a process which comprises contacting methane with an oxidative synthesizing agent under elevated pressure (e.g., 2-100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

U.S. Pat. No. 4,499,322 discloses and claims a process for the conversion of methane to higher hydrocarbons which comprises contacting methane with an oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

U.S. Pat. No. 4,499,323 discloses and claims a process for the conversion of methane to higher hydrocarbons which comprises contacting methane with a contact solid comprising a reducible oxide of praseodymium and at least one member of the group consisting of alkali metals, and compounds thereof.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. patent application Ser. No. 06/600,669 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. The entire content of this application is incorporated herein by reference.

In a typical application of the foregoing processes for the oxidative conversion of methane, methane feed is contacted with a reducible metal oxide and regeneration is accomplished separately by contacting the reduced metal oxide with an oxygen-containing gas (e.g., air). Thus, a cyclic redox process results in which methane reaction and reoxidation of the metal oxide "reagent" are performed separately and repeatedly for a continuous process.

Such a procedure presents several disadvantages for large scale continuous operation. One disadvantage is the large quantity of solid cycling between methane reaction and reoxidation in such a way that the methane and oxygen are not mixed. Another disadvantage is the necessity of developing a composition that is resistant to mechanical attrition and repeated exposure to reductive and oxidative environments.

Commonly-assigned U.S. patent application Ser. No. 06/669,551 discloses and claims a process for the conversion of methane to higher hydrocarbons by contacting methane with reducible metal oxides in the presence of oxides of nitrogen. The entire content of this application is incorporated herein by reference.

Hinsen and Baerns report studies of a continuous mode for the oxidative coupling of methane wherein regenerating air is cofed with the methane feed. Hinsen, W. and Bearns, M., "Oxidative Kopplung von Methan zu $C_2$-Kohlenwasserstoffen in Gegenwart unterschiedlicher Katalysatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600°–750° C., they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

Commonly-assigned U.S. patent application Ser. No. 06/600,656, filed Apr. 16, 1984, discloses and claims a process for the converting of methane to higher hydrocarbons which comprises contacting methane and an oxygen-containing gas with a solid comprising a reducible metal oxide and an alkali/alkaline earth metal promoter. The entire content of this application is incorporated herein by reference.

Commonly-assigned U.S. patent application Ser. No. 06/600,670, filed Apr. 16, 1984, discloses and claims a process for the converting of methane to higher hydrocarbons which comprises contacting methane and an oxygen-containing gas with a manganese silicate. The entire content of this application is incorporated herein by reference.

SUMMARY OF THE INVENTION

It has now been found that the conversion of methane to higher hydrocarbons by contacting a gas comprising methane and a gaseous oxidant with a reducible metal oxide may be improved by conducting the contacting in the presence of at least one stabilizer selected from the group consisting of chalcogens and compounds thereof. The stabilizer is at least periodically introduced with methane- and oxygen-containing gases while conducting the contacting. The contact solid comprises at least one reducible oxide of at least one metal which oxide(s) when contacted with methane at methane conversion conditions (preferably at a temperature within the range of about 500° to 1000° C.) are reduced and produce higher hydrocarbon products and water. Preferably, the contact solid further comprises at least one promoter selected from the group consisting of alkali metals, alkaline earth metals, and compounds thereof.

Chalcogens are selected from the group consisting of sulfur, selenium and tellurium. Preferred chalcogen stabilizers are sulfur and compounds thereof.

Reducible oxides include oxides of metals selected from the group consisting of Mn, Sn, In, Ge, Pb, Sb and Bi. Reducible oxides also include oxides of metals selected from the group consisting of Pr, Tb, Ce, Fe and Ru. Reducible oxides of Mn are preferred.

Alkali metals are selected from the group consisting of Li, Na, K, Rb, and Cs. Alkaline earth metals are selected from the group consisting of Mg, Ca, Sr and Ba. Mg and Ca are preferred alkaline earth promoters. However, alkali metal promoters are more preferred promoters. OF the alkali metals, lithium and sodium are preferred. Sodium is particularly preferred.

The improved process of the present invention lengthens the useful life of the solids employed resulting in a more stable process as compared to prior methods.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The gaseous oxidant is selected from the group consisting of molecular oxygen, oxides of nitrogen, and mixtures thereof. Preferably, the gaseous oxidant is an oxygen-containing gas. Air is a preferred oxygen-containing gas. Suitable oxides of nitrogen include $N_2O$, NO, $N_2O_3$, $N_2N_5$ and $NO_2$. Nitrous oxide ($N_2O$) is a presently preferred oxide of nitrogen.

The ratio of hydrocarbon feedstock to gaseous oxidant gas is not narrowly critical to the present invention. However, the ratio will desirably be controlled to avoid the formation of gaseous mixtures within the flammable region. The volume ratio of hydrocarbon/gaseous oxidant is preferably within the range of about 0.1–100:1, more preferably within the range of about 1–50:1. Methane gaseous oxidant feed mixtures containing about 50 to 90 volume % methane have been found to comprise a desirable feedstream.

The contact solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof.

Reducible oxides of cerium, praseodymium, and terbium have also been found to be effective for the conversion of methane to higher hydrocarbons, particularly when the rare earth component is associated with an alkali metal component and/or an alkaline earth metal component. Reducible oxides of iron and ruthenium are also effective, particularly when associated with an alkali or alkaline earth component.

The contact solid preferably contains, in addition to the reducible metal oxide component, at least one alkali or alkaline earth metal. The atomic ratio in which these materials are combined to form the contact solid is not narrowly critical. However, the preferred atomic ratio of the reducible oxide component (expressed as the metal, e.g., Mn) to the alkali/alkaline earth metal component (expressed as the metal, e.g., Na) may range up to about 0.10100:1, more preferably within the range of about 0.3 to 10:1.

The contact solid may optionally contain at least one phosphorus component. The amount of phosphorus contained in the contact solid is again not narrowly critical. The atomic ratio of phosphorus to the reducible oxide component (expressed as the metal, e.g., Mn) is preferably less than about 2:1. More preferably, this ratio is within the range of about 0.1–0.5:1.

The contact solid may also contain at least one halogen component. The amount of halogen contained in the contact solid is again not critical. The atomic ratio of the reducible oxide component (expressed as the metal, e.g., Mn) to the halogen component (expressed as the halogen, e.g., Cl) may range from up to about 1.5. More preferably the ratio is within the range of about 1.3 to 1000:1.

A preferred contact solid used in the process of this invention may be further expressed by the following empirical formula:

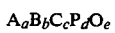

wherein A is selected from the group consisting of Mn, Sn, In, Ge, Pb, Sb, Bi, Pr, Tb, Ce, Fe, Ru and mixtures thereof; B is selected from the group consisting of F, Cl, Br, I, and mixtures thereof; C is selected from the group consisting of alkali and alkaline earth metals and mixtures thereof; a to e indicate the atomic ratio of each component; and when a is 10, b is within the range of about 0–30, c is within the range of about 0–33, d is within the range of about 0–20, and e has a value which is determined by the valence and proportions of the other elements present.

The metal components may be associated with support materials such as silica, alumina, titania, magnesia, zirconia and the like and combinations thereof. When employing agents containing rare earth components—oxides of Ce, Pr, and Tb—the rare earth oxides preferably serve as supports. Similarly, when employing oxides of Fe and Ru, those oxides preferably serve as supports.

Reducible oxides of manganese have been found to be particularly desirable for methane conversion according to the method of the present invention when associated with an alkali metal (preferably sodium). Particularly preferred agents comprise silica- and/or magnesia-supported solids containing oxides of manganese and sodium.

The solid can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkaline metal or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300° to 1200° C. Particular calcination temperatures will vary depending upon the particular metal compound or compounds employed.

Preferably, methane and oxygen are contacted with the agent in the substantial absence of catalytically effective nickel, noble metals and compounds thereof. (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Chalogen stabilizers are introduced with the gaseous feedstreams flowing to the process. Suitable stabiliziers include free chalogen gas or a chalogen compound. Suitable chalogen compounds include hydrogen chalcogenides, chalcogen oxides, ammonium, chalogenides, aliphatic chalcogenides (e.g., methyl sulfide, methylene sulfide, ethyl sulfide, amyl sulfide and allyl sulfide) cycloaliphatic chalcogenides (e.g., cyclohexyl sulfide), chalcogen substituted aliphatic acids, amine chalcogenide, salts, and the like. Presently preferred chalcogen stabilizers are sulfur and compounds thereof, especially methyl sulfide, hydrogen sulfide and sulfur dioxide.

The amount of stabilizer introduced is preferably such that the stabilizer content of the combined gaseous feedstreams (e.g., stabilizer, gas comprising methane, and gaseous oxidant) is less than about 1 vol. %, more preferably within the range of about 1 ppm to 1 vol. %, still more preferably within the range of about 10 to 1000 ppm. Optimum quantities are dependent on the stabilizer selected, the particular contact solid employed and on the process temperature.

Because the stabilizer may form deactiviting species on the contact solid, operating temperatures for the method of this invention are selected to be exceed the decomposition temperatures of such species. While not wishing to be bound by any theory of operability, it appears that the stabilizer reacts with the reducible metal oxide component of the contact solid. For example, sulfur stabilizers react with Mn components to form sulfates, resulting in relatively rapid solid deactivation. As shown in the following examples, however, by raising the operating temperatures to a suitable level, the deactivating effect is overcome, presumably by sulfate decomposition at the higher temperatures. While selection of a similar operating temperature thus requires some degree of experimentation, such selection is within the skill of the art.

Operating temperatures are generally selected within the range of about 300° to 1200° C., more preferably within the range of about 500° to 1000° C.

If reducible oxides of metals such as In, Ge or Bi are present in the solid, the particular temperature selected may further depend on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 hr $^{-1}$, more preferably within the range of about 600 to 40,000 hr $^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the gaseous oxidant cofed with methane to the contact zone.

The contact solids may be maintained in the contact zone as fixed, moving, or fluidized beds of solids. A fixed bed of solids is currently preferred for the method of this invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following example. Experimental results reported below include conversions and selectivities calculated on a carbon mole basis.

EXAMPLE

A contact solid consisting of 12.5 wt. % $NaMnO_4$ on magnesia was prepared by impregnating the MgO support with appropriate amount of sodium permanganate and drying and calcining the resulting solid. An alumina reactor (12 mm. inside diameter) was charged with 5 ml. of the calcined solids and the reactor was heated to reaction temperature with a stream of heated nitrogen. Results obtained when a methane/air feed containing 50 vol. % air and 0.005 vol. % $SO_2$ were contacted with the solid are shown in the following table. The run was performed at a $CH_4$ GHSV of 3600 hr.$^{-1}$.

In a similar run performed at a temperature of 800° C., methane conversion and $C_2+$ selectivity decreased to 1.2% and 64.2%, respectively, at the end of a run time of 33 hours.

As indicated by the table, the $NaMnO_4/MgO$ system was extremely sensitive to temperature variation in the vivcinity of 900° C., slight upward adjustments resulting in the maintenance of stable performance over time.

TABLE

| Run time (hours) | Temp. (°C.) | % $CH_4$ Conv. | % Selectivity to: | | | | |
|---|---|---|---|---|---|---|---|
| | | | $C_2=$ | $C_2$ | $C_2+$ | CO | $CO_2$ |
| 26 | 902 | 27.6 | 41.1 | 21.6 | 68.9 | 8.5 | 22.7 |
| 118 | 900 | 16.8 | 41.5 | 23.1 | 68.7 | 22.5 | 8.8 |
| 262 | 900 | 16.1 | 40.8 | 22.5 | 67.6 | 25.1 | 7.4 |
| 310 | 920 | 25.7 | 42.6 | 14.8 | 62.8 | 26.0 | 11.2 |
| 358 | 929 | 24.8 | 39.0 | 21.3 | 66.1 | 3.7 | 30.3 |
| 478 | 912 | 18.7 | 42.2 | 20.7 | 68.0 | 24.9 | 7.1 |
| 550 | 910 | 17.3 | 42.1 | 22.4 | 69.6 | 23.3 | 7.1 |
| 646 | 915 | 19.9 | 42.7 | 18.6 | 66.1 | 26.5 | 7.4 |
| 694 | 914 | 22.8 | 42.7 | 20.0 | 68.1 | 23.7 | 8.3 |
| 718 | 915 | 22.0 | 44.4 | 18.4 | 68.2 | 23.3 | 8.5 |
| 790 | 913 | 20.7 | 43.4 | 18.5 | 67.0 | 24.9 | 8.1 |
| 814 | 916 | 27.3 | 41.3 | 19.1 | 66.5 | 4.5 | 29.0 |

What is claimed is:

1. In an improved method for converting methane to higher hydrocarbon products and coproduct water wherein a gas comprising methane and a gaseous oxidant are contacted with a solid comprising at least one reducible oxide of at least one metal which oxide when contacted with methane at a temperature within the range of about 500° to 1000° C. is reduced and produces higher hydrocarbon products and water, the improvement which comprises contacting at a a temperature selected within the range of about 300° to 1200° C. in the presence of at least one stabilizer selected from the group consisting of chalcogens and compounds thereof.

2. The method of claim 1 wherein the stabilizer is selected from the group consisting of sulfur and compounds thereof.

3. The method of claim 1 wherein the stabilizer is $SO_2$.

4. The method of claim 1 wherein the stabilizer is $H_2S$.

5. The method of claim 1 wherein the stabilizer is an aliphatic sulfide.

6. The method of claim 5 wherein the stabilizer is methyl sulfide.

7. The method of claim 1 wherein the solid comprises a reducible oxide of Mn.

8. The method of claim 1 wherein the solid further comprises at least one member of the group consisting of alkali metals, alkaline earth metals and compounds thereof.

9. The method of claim 1 wherein the solid further comprises at least one member of the group consisting of alkali metals and compounds thereof.

10. The method of claim 1 wherein the solid further comprises at least one member of the group consisting of sodium and compounds thereof.

11. The method of claim 1 wherein the solid further comprises at least one member of the group consisting of lithium and compounds thereof.

12. The method of claim 9 wherein the solid comprises a reducible metal oxide component and an alkali metal component associated with a support.

13. The method of claim 12 wherein the support comprises silica.

14. The method of claim 12 wherein the support comprises magnesia.

15. The method of claim 1 wherein the gaseous oxidant is an oxygen-containing gas.

16. The method of claim 1 wherein the gaseous oxidant comprises molecular oxygen.

17. The method of claim 1 wherein the gaseous oxidant comprises oxides of nitrogen.

18. The method of claim 17 wherein the oxides of nitrogen comprise $N_2O$.

* * * * *